Feb. 4, 1964 C. FISCHER Plant Pat. 2,357
GLADIOLUS PLANT
Filed Oct. 16, 1962
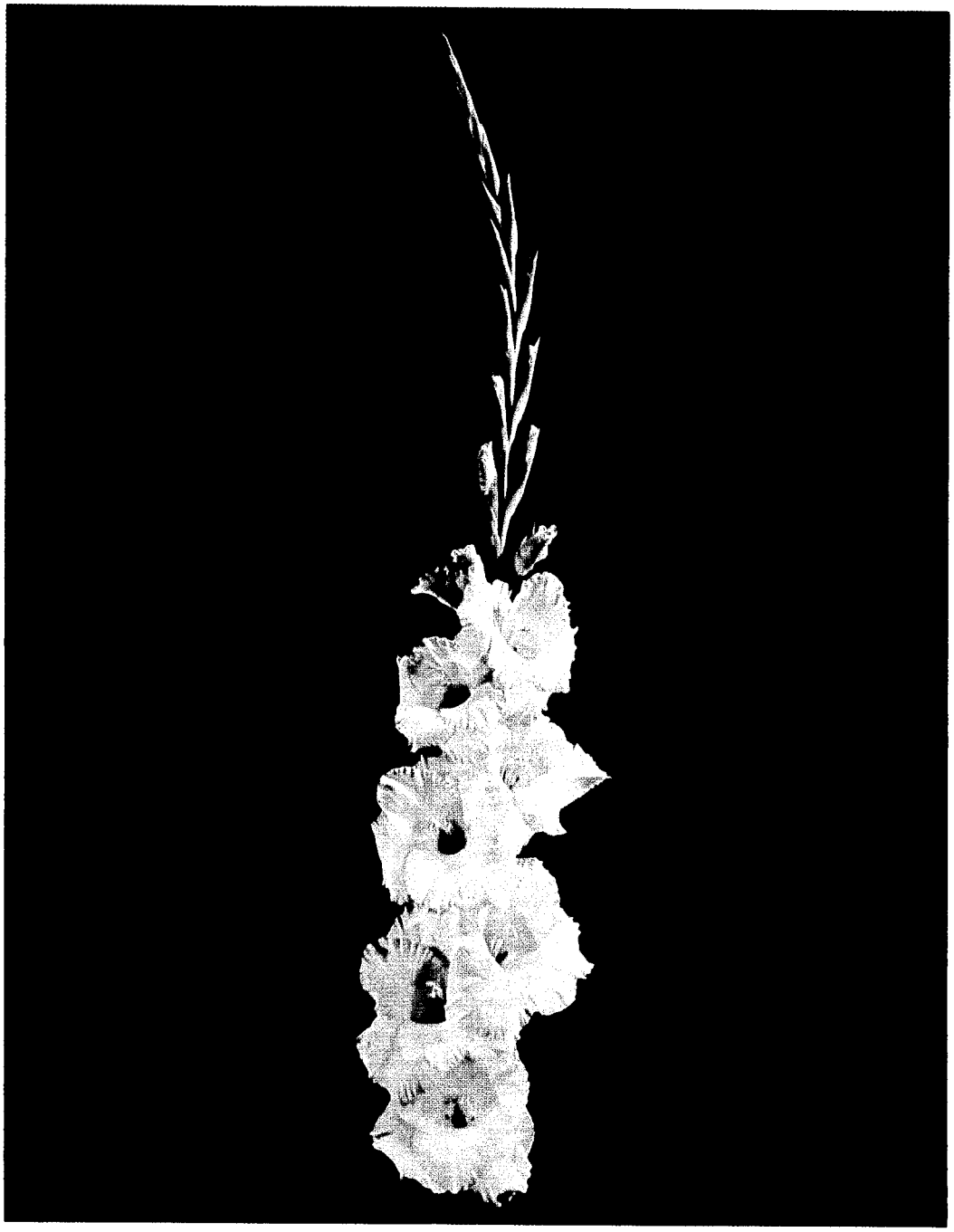
Inventor.
Carl Fischer
By: Robb & Robb
Attorneys.

United States Patent Office

Plant Pat. 2,357
Patented Feb. 4, 1964

2,357
GLADIOLUS PLANT

Carl Fischer, St. Charles, Minn., assignor to Imperial Flowers Limited, Leamington, Ontario, Canada, a corporation of Canada Filed Oct. 16, 1962, Ser. No. 231,051
1 Claim. (Cl. Plt.—85)

The present invention relates to a new and distinct variety of gladiolus plant which was originated by me by crossing the variety known as "Minaret" (unpatented) with the variety "Apple Blossom" (Plant Patent No. 1,517), the former being the seed parent and the latter being the pollen parent. This cross was made as a part of an extensive series conducted by me in my breeding fields at St. Charles, Minnesota.

As the result of this breeding, I have produced a new and improved gladiolus variety which is endowed with a unique combination of characteristics which distinguish it from its parents, as well as from all other varieties of which I am aware, as evidenced by the following features which are outstanding therein:

(1) The ability of the florets to open well from tight buds;

(2) Good temperature tolerance; and (3) A distinctive and attractive Fuchsine Pink general color tonality of the flower petals which have a delicate pink edging, said flowers having white throats and midribs, and the flowers sometimes being flecked on the reverse of the petals with Fuchsine Pink.

My new variety more nearly resembles the pollen parent "Apple Blossom" than any other variety, but differs principally therefrom by being less prolific than "Apple Blossom," a later bloomer, and a better flower opener from tight buds.

Asexual reproduction of my new variety by cormels through several generations, as performed by me at St. Charles, Minnesota, shows that the foregoing characteristics and distinctions come true to form and are established and transmitted through succeeding propagations.

The accompanying drawing shows a typical specimen flower spike of my new variety, with the flowers in different stages of development ranging from closed buds through partially open buds to fully open flowers, as depicted in color as nearly true as it is reasonably possible to make the same in a color illustration of this character.

The following is a detailed description of my new variety, with color terminology in accordance with the Horticultural Colour Charts issued by the British Colour Council and the Royal Horticultural Society, except where general color terms of ordinary dictionary significance are obvious:

Locality where grown and observed: St. Charles, Minnesota.

Propagation: Holds its distinguishing characteristics through succeeding propagations by plantings derived from cormels.

*Plant*

Growth: Rugged; excellent propagator; average height ranges from about 58 inches to 60 inches.

Blooming habit: Mid-season bloomer in the Northern latitudes of the United States; comes into bloom from large bulbs in from about 80 to 85 days.

Stems: Long; willowy.

*Diameter at base.*—About ⅜ inch.

*Color (just above bulb).*—Mallow Purple, Plate 630.

Foliage: Semi-drooping; leaves average about 34 inches tall and about 1½ inches wide. Color—healthy green.

Disease resistance: Unusually good resistance to Septoria leaf spot and average resistance to Fusarium yellows and Sclerotina dry rot, as determined by comparison with other varieties grown in my fields near St. Charles, Minnesota, in irrigated black loam soil.

Corms (bulbs): Round; plump; smooth; average diameter ranges from about 2 inches to 2½ inches; high-crowned and well-husked. Color of flesh—between Amber Yellow, Plate 505/1 and Amber Yellow, Plate 505/2.

*Flower*

Spike: Tall; bears from 20 to 22 buds, with from 7 to 9 buds opening at once and 6 or 7 buds showing color; flowerhead ranges from about 24 inches to 26 inches long.

Bud:

*Size.*—About 2½ inches long when opening.

*Opening.*—Opens well; 6 or 7 buds show color at one time.

Flower:

*Arrangement.*—Florets are semi-formally arranged on the stem and usually all face forward.

*Size.*—Lower florets average from about 5 inches to 5½ inches in diameter, with upper florets being progressively smaller.

*Form.*—Florets are round, recurved and slightly ruffled.

*Keeping qualities.*—Keeps well.

Petals:

*Shape.*—Round; moderately ruffled; recurved.

*Size.*—Upper petals—about 2¼ inches wide. Lip petal—about 1½ inches wide.

*Aspect.*—Average substance; smooth surface.

*Fragrance.*—None.

*Color.*—Fuchsine Pink, Plate 627/1 at edges of petals, blending to Fuchsine Pink, Plate 627/3 on upper petals, with general color effect of Fuchsine Pink, Plate 627/2; white throat and midribs; the florets are sometimes flecked on reverse of petals with Fuchsine Pink, Plate 627; calyx Fuchsine Pink, Plate 627.

*Reproductive Organs*

Stamens: Color—light purple.

Pistil: Color—white.

I claim:

A new and distinct variety of gladiolus plant, substantially as herein shown and described, characterized particularly as to novelty by the unique combination of an ability of the flowers to open well from tight buds, good temperature tolerance, and a distinctive and attractive general color tonality of the flower petals corresponding to Fuchsine Pink, said petals having a delicate pink edging, and the individual florets having white throats and midribs, and with the florets sometimes flecked on the reverse of the petals with Fuchsine Pink.

No references cited.